United States Patent [19]
Kohmura et al.

[11] Patent Number: 4,830,278
[45] Date of Patent: May 16, 1989

[54] STEAM STERILIZING APPARATUS

[75] Inventors: Kisaburo Kohmura, Aichi; Haruo Nishi; Masanari Takagi, both of Mie, all of Japan

[73] Assignee: Nissen Corporation, Aichi, Japan

[21] Appl. No.: 238,263

[22] Filed: Aug. 30, 1988

[30] Foreign Application Priority Data

Sep. 12, 1987 [JP] Japan .................. 62-228782
Sep. 12, 1987 [JP] Japan .................. 62-228783

[51] Int. Cl.$^4$ .............................................. A23L 1/00
[52] U.S. Cl. .......................................... 99/468; 99/359; 99/475; 99/483; 99/487; 99/516; 422/105; 422/302; 426/407; 426/521
[58] Field of Search ........... 99/275, 468, 473–476, 99/486, 470, 487, 483, 453, 359, 361, 362, 516; 422/25, 105, 114, 302, 304; 426/397, 407, 412, 521

[56] References Cited

U.S. PATENT DOCUMENTS

| | | | |
|---|---|---|---|
| 3,778,521 | 12/1973 | Fisher et al. | 99/516 X |
| 3,897,210 | 7/1975 | Gruber et al. | 99/474 X |
| 4,164,590 | 8/1979 | Mencacci | 426/407 |
| 4,179,986 | 12/1979 | Mencacci | 99/359 |
| 4,279,858 | 7/1981 | Huling | 422/302 X |
| 4,331,629 | 5/1982 | Huling | 422/105 X |
| 4,385,035 | 5/1983 | Akitoshi et al. | 99/483 X |
| 4,441,406 | 4/1984 | Becker et al. | 426/521 X |
| 4,446,778 | 5/1984 | Cipelletti | 99/486 X |
| 4,773,321 | 9/1988 | Wijts | 99/468 |

Primary Examiner—Timothy F. Simone
Attorney, Agent, or Firm—Dennison, Meserole, Pollack & Scheiner

[57] ABSTRACT

Apparatus for sterilizing packed foods includes a sterilizing chamber for storing packed foods therein, a jet pipe mounted on the interior upper portion of the sterilizing chamber for jetting mixture of steam and compressed air, an ejector having an inlet port, a suction port and an outlet port and connected at the outlet port to the jet pipe for generating a suction force through a flow of mixture of steam and compressed air, a steam line connected to the inlet port of the ejector for supplying steam thereto, a circulation line connected at one end to the interior lower portion of the sterilizing chamber and at the other end to the suction part of the ejector, a drain line connected to the bottom of the sterilizing chamber for exhausting a part of the mixture of steam and compressed air, a heat exchanger interposed between the sterilizing chamber and the drain line, and a compressed air line connected to the inlet port of the ejector through the heat exchanger.

2 Claims, 2 Drawing Sheets

STEAM STERILIZING APPARATUS

BACKGROUND OF THE INVENTION

1. Field of the Invention

The present invention relates to apparatus for sterilizing foods packed in retort pouches, trays, cups, bottles, cans or the like by high-temparature and high-pressure steam.

2. DESCRIPTION OF THE PRIOR ART

Such sterilizing apparatus may include a sterilizing chamber to which a steam line and a compressed air line are connected. The sterilizing chamber also includes a drain line connected to the bottom thereof. Steam and compressed air are supplied into the sterilizing chamber through the steam line and the compressed air line, respectively. Then, a part of the mixture of steam and compressed air is exhausted from the drain line, so that the sterilizing chamber is maintained at high temperature and high pressure to sterilize packed foods stored therein.

In such conventional sterilizing apparatus, it is sometimes difficult to uniform the temperature distribution in the interior of the sterilizing chamber; there tends to be temperature differences among the upper, central and lower portions of the interior of the sterilizing chamber. The variations in the temperature difference may sometimes cause inadequate sterilization of the packed foods located in the lower and central portions of the sterilizing chamber.

Further, in such conventional sterilizing apparatus, when the temperature in the sterilizing chamber becomes lower than the predetermined temperature, steam is supplied from the steam line, irrespective of the pressure therein. In some cases, therefore, the pressure in the sterilizing chamber becomes higher than a predetermined value, which may cause undesirable deformation of the packed foods.

SUMMARY OF THE INVENTION

It is, accordingly, an object of the present invention to provide steam sterilizing apparatus which uniforms the temperature distribution in the sterilizing chamber.

It is another object of the present invention to provide steam sterilizing apparatus which maintain the sterilizing chamber at a predetermined pressure at all times.

According to the present invention, there is provided apparatus for sterilizing packed foods which comprises a sterilizing chamber for storing packed foods therein, a jet pipe mounted on the interior upper portion of the sterilizing chamber for jetting mixture of steam and compressed air, an ejector having an inlet port, a suction port and an outlet port and connected at the outlet port to the jet pipe for generating a suction force through a flow of mixture of steam and compressed air, a steam line connected to the inlet port of the ejector for supplying steam thereto, a circulation line connected at one end to the interior lower portion of the sterilizing chamber and at the other end to the suction port of the ejector, a drain line connected to the bottom of the sterilizing chamber for exhausting a part of the mixture of steam and compressed air, a heat exchanger interposed between the sterilizing chamber and the drain line, and a compressed air line connected to the inlet port of the ejector through the heat exchanger.

Preferably, the sterilizing apparatus further includes a pressure sensor mounted within the sterilizing chamber for detecting pressure in the sterilizing chamber and an exhaust valve connected to the drain line and operative to control the exhaust amount of the mixture in response to a detection signal from the pressure sensor so as to maintain the sterilizing chamber at a predetermined pressure.

With the construction described above, mixture of steam and compressed air is jetted from the jet pipe disposed at the interior upper portion of the sterilizing chamber, so that a suction force may be produced at the suction port of the ejector. By means of the suction force, a circulation passage is formed through the interior lower portion of the sterilizing chamber, the circulation line, the ejector, and the jet pipe. Then, a part of the mixture of steam and compressed air in the sterilizing chamber is circulated in the circulation passage, so that an air stream is produced in the sterilizing chamber, thereby uniforming the temperature distribution in the sterilizing chamber.

The compressed air in the compressed air line is preheated by exhaust heat of the mixture in the heat exchanger and is fed to the ejector, thereby permitting more improved uniformity of the temperature distribution in the sterilizing chamber and increasing the efficiency of sterilizing operation.

Further, when the pressure in the sterilizing chamber becomes above the predetermined value, the exhaust valve in the drain line is controlled to be opened and closed in response to a detection signal from the pressure sensor to allow discharge of the mixture of steam and compressed air, so that the sterilizing chamber may be maintained at the predetermined pressure.

The present invention will become more fully apparent from the claims and description as it proceeds in connection with the drawings.

DETAILED DESCRIPTION OF A PREFERRED EMBODIMENT

Figure 1:
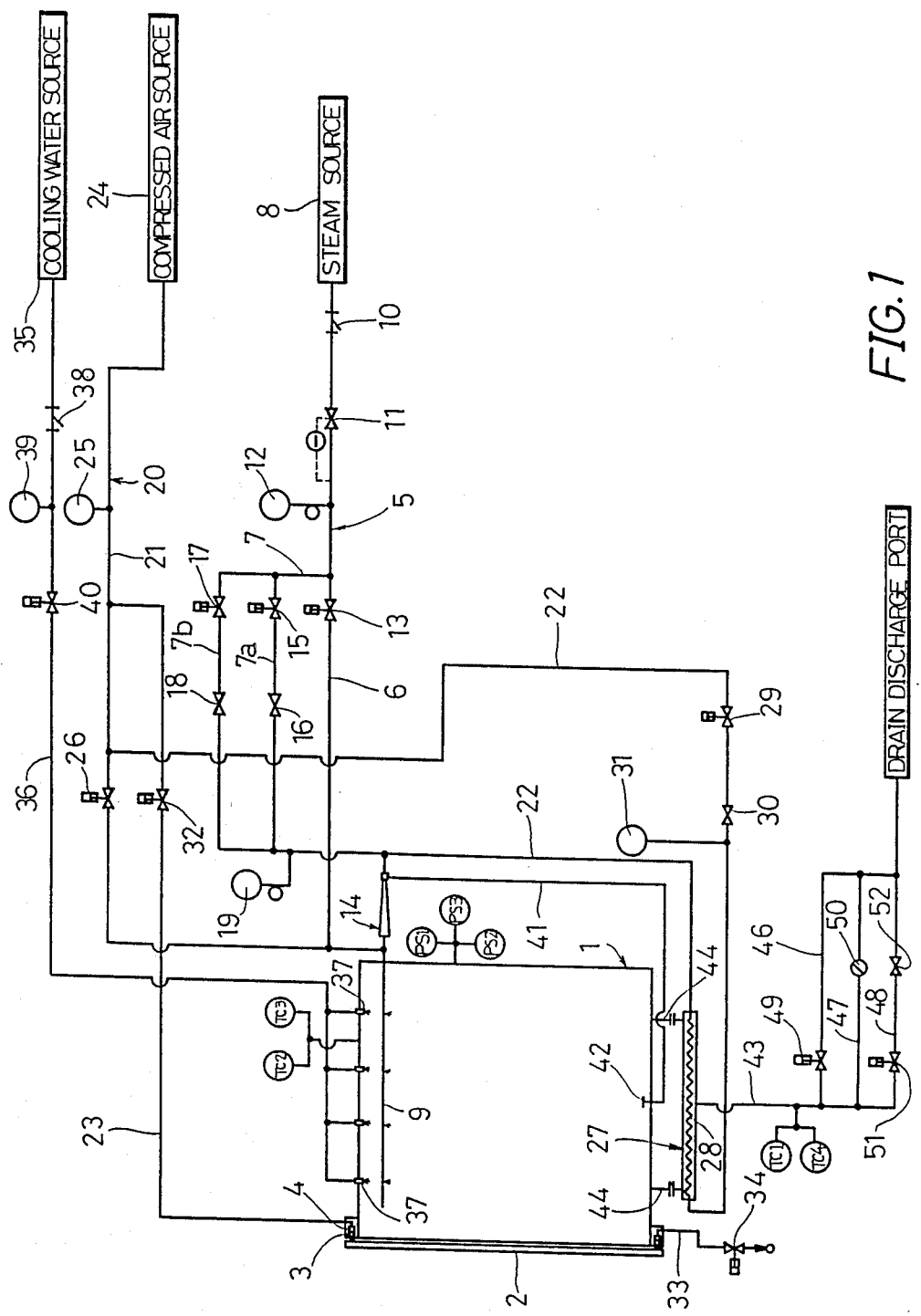
FIG. 1 is a diagrammatic view of steam sterilizing apparatus according to a preferred embodiment of the present invention.

Referring now to the drawings, FIG. 1 diagrammatically illustrates a sterilizing chamber 1 of generally box-shaped configuration having an open end. An access door 2 is movably mounted to the open end of the sterilizing chamber 1 for loading and unloading packed foods. At the interface between the sterilizing chamber 1 and the access door 2, a gasket 3 is provided to maintain air-tightness of the interface. The gasket 3 has a seal chamber 4 formed therein.

The sterilizing chamber 1 has connected thereto a steam line 5, a compressed air line 20, a cooling water line 36, a circulation line 41 and a drain line 43.

The steam line 5 is composed of a main steam line 6 and a bypass steam line 7. The main steam line 6 is connected at one end to a steam source 8 and at the other end to one end of a jet pipe 9 disposed in the upper portion of the interior of the sterilizing chamber 1. The main steam line 6 is provided with a strainer 10, a pressure reducing valve 11, a pressure gauge 12 and a main steam valve 13 disposed in sequence from the steam source 8 toward the jet pipe 9.

Figure 2:
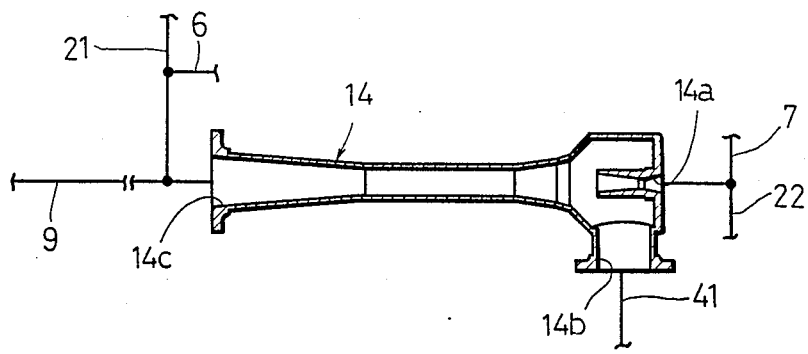
FIG. 2 is a sectional view of the ejector.

The bypass steam line 7 is branched from the main steam line 6 at a portion between the pressure gauge 12 and the main steam valve 13 and is connected to an ejector 14, as shown in FIG. 2. The ejector 14 has an inlet port 14a connected to the bypass steam line 7, a suction port 14b connected to the circulation line 41 and an outlet port 14c connected to the one end of the jet pipe 9. The ejector 14 serves to generate a suction force at the suction port 14b through mixture of steam and compressed air flowing through a passage thereof.

The bypass steam line 7 is divided into a first and a second branch pipe 7a and 7b at the medial portion thereof. The first branch pipe 7a is provided with a first bypass steam valve 15 and a throttle adjusting valve 16, while the second branch pipe 7b is provided with a second bypass steam valve 17 and a throttle adjusting valve 18. The bypass steam line 7 is further provided with a pressure gauge 19 downstream of the first and second branch pipes 7a and 7b.

The compressed air line 20 is composed of a main compressed air line 21, a bypass compressed air line 22 and a seal air line 23. The main compressed air line 21 is connected at one end to a compressed air source 24 and at the other end to the one end of the jet pipe 9 along with the main steam line 6. The main compressed air line 21 is provided with a pressure gauge 25 and a main compressed air valve 26 disposed in sequence from the compressed air source 24 toward the jet pipe 9.

Figure 3:
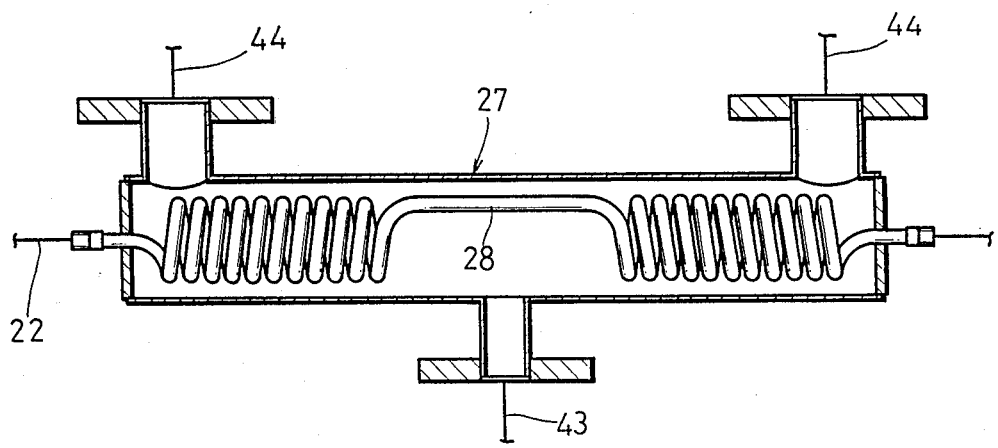
FIG. 3 is a sectional view of the heat exchanger.

A bypass compressed air line 22 is branched from the main compressed air line 21 at a portion between the pressure gauge 25 and the main compressed air valve 26. As shown in FIG. 3, the bypass compressed air line 22 is connected through a coil tube 28 of a heat exchanger 27 to the inlet port 14a of the ejector 14. The bypass compressed air line 22 is provided with a bypass compressed air valve 29, a throttle adjusting valve 30 and a pressure gauge 31 disposed in sequence from a junction with the main compressed air line 21 toward the coil tube 28 of the heat exchanger 27.

The seal air line 23 is branched from the main compressed air line 21 at a portion between the pressure gauge 25 of the main compressed air line 21 and a junction thereof with the bypass compressed air line 22, and is connected to the seal chamber 4 of the gasket 3. The seal air line 23 is provided with a seal air inlet valve 32. The seal chamber 4 of the gasket 3 is connected to an air bleed pipe 33 which is provided with an air bleed valve 34.

The cooling water line 36 is connected at one end to a cooling water source 35 and at the other end to spraying nozzles 37 provided along the ceiling of the sterilizing chamber 1. The cooling water line 36 is provided with a strainer 38, a pressure gauge 39 and a cooling water valve 40 disposed in sequence from the cooling water source 35 toward the spraying nozzles 37.

The circulation line 41 is connected at one end to an outlet port 42 provided at the bottom of the sterilizing chamber 1 and at the other end to the suction port 14b of the ejector 14, as shown in FIG. 2.

As shown in FIGS. 1 and 3, the drain line 43 is connected at one end through a heat exchanging chamber of the heat exchanger 27 to drain ports 44 provided at the bottom of the sterilizing chamber 1 and at the other end to a drain discharge port 45. The drain line 43 is divided into a first, a second and a third branch pipe 46, 47 and 48 at the medial poriton thereof. The first branch pipe 46 is provided with a main exhaust valve 49, the second branch pipe 47 is provided with a steam trap 50, and the third branch pipe 48 is provided with a bypass exhaust valve 51 and a throttle adjusting valve 52 adapted for preventing the pressure in the sterilizing chamber 1 from becoming above a predetermined value.

The sterilizing chamber 1 is provided with a first, a second and a third pressure sensor PS1, PS2 and PS3 for detecting pressure in the sterilizing chamber 1 and is also provided with a second and a third temperature sensor TC2 and TC3 for detecting temperature therein.

The drain line 43 is provided with a first and a fourth temperature sensor TC1 and TC4 for detecting the drain temperature.

Detection signals from the first to third pressure sensors PS1 to PS3 and detection signals from the first to fourth temperature sensors TC1 and TC4 are fed into a control unit. Then, output signals from the control unit are used to control opening and closing operation of the above described valves so as to achieve several steps which will be described below.

The sterilizing steps of the apparatus thus constructed will be explained in relation to the case of retort pouches.

(1) Loading Step

A carriage having a plurality of shelves arranged one above another is used to load, into the sterilizing chamber 1, retort pouches placed side by side on each shelf.

(2) Preheating Step

After the packed foods have been loaded into the sterilizing chamber 1, the access door 2 of the sterilizing chamber 1 is closed and the main steam valve 13 is opened, so that steam from the steam source 8 is fed through the strainer 10, the pressure reducing valve 11 and the main steam valve 13 in the main steam line 6 in sequence into the jet pipe 9 in the sterilizing chamber 1 and is jetted from a plurality of jet holes of the jet pipe 9. At this time, the main exhaust valve 49 is also opened to discharge air in the sterilizing chamber 1 through the drain ports 44, the heat exchanging chamber of the heat exchanger 27 and the main exhaust valve 49 in sequence.

In the above described condition, the sterilizing chamber 1 and the packed foods loaded therein is preheated, until the temperature in the sterilizing chamber 1 reaches a predetermined temperature, for example, 70° C.

Simultaneously with start of this step, the seal air inlet valve 32 is opened to cause compressed air supplied from the compressed air source 24 to flow through a portion of the main compressed air line 21 into the seal air line 23. The compressed air is then fed through the seal air inlet valve 32 into the seal chamber 4 of the gasket 3 thereby to ensure air-tightness of the contact area between the sterilizing chamber 1 and the access door 2. In the preheating step, all of the valves except the main steam valve 13, the main exhaust valve 49 and the seal air inlet valve 32 are closed.

(3) First Temperature Raising Step

When the temperature of the drain line 43 becomes above the predetermined temperature of 70° C., the first temperature sensor TC1 in the drain line 43 generates a detection signal to close the main exhaust valve 49 and the main steam valve 13 and, at the same time, open the first and second bypass steam valves 15 and 17 and the bypass compressed air valve 29.

Thereupon, the steam supplied from the steam source 8 is fed through the strainer 10 and the pressure reducing valve 11 in the main steam line 6 into the bypass steam line 7. Then, the steam flows through the first and second bypass steam valves 15 and 17 and the throttle adjusting valves 16 and 18 of the first and second branch pipes 7a and 7b, and then through the ejector 14 to be jetted from the jet holes of the jet pipe 9 into the sterilizing chamber 1.

At this time, the compressed air supplied from the compressed air source 24 is fed through the main compressed air line 21 into the bypass compressed air line 22. Then, the compressed air flows through the bypass compressed air valve 29, the throttle adjusting valve 30 and the coil tube 28 of the heat exchanger 27 and is mixed with the steam at the inlet port 14a of the ejector 14. Thereafter, the compressed air flows through the ejector 14 and is jetted from the jet holes of the jet pipe 9 into the sterilizing chamber 1.

The mixture of steam and compressed air flowing through the ejector 14 generates a suction force at the suction port 14b of the ejector 14. Under the action of the suction force, a part of the mixture of steam and compressed air in the sterilizing chamber 1 is sucked out from the outlet port 42 at the bottom thereof, flows through the circulation line 41 to be sucked in through the suction port 14b of the ejector 14 and flows through the ejector 14 to be jetted from the jet holes of the jet pipe 9 into the sterilizing chamber 1, thus completing circulation. This produces a circulating air flow in the sterilizing chamber 1, which reduces variations in the temperature distribution in the sterilizing chamber 1.

A part of the mixture in the sterilizing chamber 1 flows from the drain ports 44 through the heat exchanging chamber of the heat exchanger 27 in the drain line 43 and is discharged through the steam trap 50 in the second branch pipe 47.

The compressed air flowing through the bypass compressed air line 22 is preheated by exhaust heat of the above mixture at the coil tube 28 of the heat exchanger 27, and then fed to the ejector 14. This causes temperature in the sterilizing chamber 1 to rise rapidly and also assists further reduction of variations in the temperature distribution in the sterilizing chamber 1.

In the above described condition, the temperature in the sterilizing chamber 1 is increased to a predetermined temperature, for example, 80° C.

In this step, when pressure in the sterilizing chamber 1 becomes above a predetermined value, that is, when it reaches a predetermined value of 0.2 kgf/cm²G (gauge pressure at a pressure of 0 atm)+0.05 kgf/cm²G for example, the first pressure sensor generates a detection signal to effect opening-closing (on-off) control of the bypass exhaust valve 51 in the drain line 43, so that the pressure in the sterilizing chamber 1 may be maintained within the range from the predetermined value of 0.2 kgf/cm²G to 0.2 kgf/cm²G+0.05 kgf/cm²G.

(4) First Sterilizing Step

When the temperature in the sterilizing chamber 1 reaches the predetermined temperature of 80° C., the second temperature sensor TC2 generates a detection signal to effect opening-closing (on-off) control of the first and second bypass steam valves 15 and 17 to intermittently supply steam into the sterilizing chamber 1, so that the temperature in the sterilizing chamber 1 may be maintained at the predetermined temperature of 80° C.

The pressure in the sterilizing chamber 1 may be maintained at the predetermined value in the same manner as described in the first temperature raising step.

With the temperature in the sterilizing chamber 1 at the predetermined value of 80° C. and the pressure therein at the predetermined value of 0.2 kgf/cm²G, the first sterilization of the packed foods is effected for a period of time set by a timer, for example, 15 minutes.

(5) Second Temperature Raising Step

After the duration set by the timer has elapsed, the first and second bypass steam valves 15 and 17 are held open to continuously supply mixture of steam and compressed air into the sterilizing chamber 1 in the same manner as described in the first temperature raising step, so that the temperature in the sterilizing chamber 1 may be increased to a predetermined temperature, for example, 110° C.

In this step, when the pressure in the sterilizing chamber 1 becomes above a predetermined pressure, that is, when it reaches a predetermined pressure of 1.0 kgf/cm²G+0.08 kgf/cm²G for example, the second pressure sensor PS2 generates a detection signal to effect opening-closing control of the bypass exhaust valve 51, so that the pressure in the sterilizing chamber 1 may be maintained within the range from the predetermined value of 1.0 kgf/cm²G to 1.0 kgf/cm²G+0.08 kgf/cm²G.

(6) Second Sterilizing Step

When the temperature in the sterilizing chamber 1 reaches the predetermined temperature of 110° C., the third temperature sensor TC3 generates a detection signal to effect opening-closing (on-off) control of the first and second bypass steam valves 15 and 17 to intermittently supply steam into the sterilizing chamber 1, so that the sterilizing chamber 1 may be maintained at the predetermined temperature of 110° C.

The pressure in the sterilizing chamber 1 may be maintained at the predetermined pressure in the same manner as described in the second temperature raising step.

With the temperature in the sterilizing chamber 1 at the predetermined value of 110° C. and the pressure therein at the predetermined value of 1.0 kgf/cm²G, the second sterilization of the packed foods is effected for a period of time set by a timer, for example, 15 minutes.

(7) Cooling Step

When the duration set by the timer has elapsed, the first and second bypass steam valves 15 and 17 are closed to stop supply of steam into the sterilizing chamber 1. At the same time, the bypass compressed air valve 29 is closed and the main compressed air valve 26 is opened.

The compressed air supplied from the compressed air source 24 flows through the main compressed air valve 26 in the main compressed air line 21 and jets from the jet holes of the jet pipe 9 in the sterilizing chamber 1.

When the pressure in the sterilizing chamber 1 becomes above a predetermined value, that is, when it reaches a predetermined value of 1.25 kgf/cm²G+0.05 kgf/cm²G for example, the third pressure sensor PS3 generates a detection signal to effect opening-closing (on-off) control of the main compressed air valve 26, so that the pressure in the sterilizing chamber 1 may be maintained within the range from the predetermined value of 1.25 kgf/cm²G to 1.25 kgf/cm²G+0.05 kgf/cm²G.

After 40 to 60 seconds from start of the cooling step, the cooling water valve 40 is controlled to be alternately opened and closed every several seconds. Cooling water supplied from the cooling water source 35 into the cooling water line 36 flows through the cooling water valve 40 to be intermittently sprayed from the spraying nozzles 37 in the sterilizing chamber 1. This prevents abrupt reduction of pressure in the sterilizing chamber 1, thereby avoiding any possible damage to the containers of the packed foods.

After the packed foods have been cooled by the intermittent spraying of water for several minutes, the cooling water valve 40 is held open, permitting continuous spraying of water from the spraying nozzles 37 in the sterilizing chamber 1. This causes rapid cooling of the packed foods. A part of the cooling water sprayed into the sterilizing chamber 1 flows through the drain pipe 43.

Thus, the sterilizing chamber 1 is cooled, until the temperature therein becomes below a predetermined temperature, for example, 50° C.

When the temperature in the drain line 43 becomes below the predetermined temperature of 50° C., the fourth temperature sensor TC4 in the drain line 43 generates a detection signal to close the main compressed air valve 26, the cooling water valve 40 and the seal air inlet valve 32, and at the same time, to open the main exhaust valve 49 and the air bleed valve 34.

(8) Unloading Step

As the main exhaust valve 49 is opened, the pressure in the sterilizing chamber 1 is reduced, and when it substantially reaches the atmospheric pressure, the access door 2 is opened and the packed foods on the carriage are taken out of the sterilizing chamber 1. Now, the sterilizing process for the packed foods is all completed.

As described above, in this embodiment the bypass exhaust valve 51 is controlled to be opened and closed in response to the detection signal from the first pressure sensor PS1 or the second pressure sensor PS2 in the first temperature raising step, the first sterilizing step, the second temperature raising step and the second sterilizing step so as to maintain the pressure in the sterilizing chamber at a predetermined pressure (saturated steam pressure+0.2 to 0.7 kgf/cm$^2$G). Therefore, packed foods may be sterilized under the optimum pressure condition, thereby preventing any possible damage to or deformation of the packed foods due to variations in pressure in the sterilizing chamber 1.

Furthermore, in this embodiment, mixture of steam and compressed air in the sterilizing chamber 1 is circulated through the circulation line 41 under the action of suction force generated by steam and compressed air flowing through the ejector 14, permitting reduction of variations in the temperature distribution in the sterilizing chamber 1 and consequently assuring substantial uniformity of the temperature distribution therein. Therefore, the packed foods placed on each shelf of the carriage may be heat treated without any inadequate sterilization.

The compressed air in the compressed air line 22 is preheated substantially up to the drain temperature by exhaust heat of the mixture in the heat exchanger 27. Then, the compressed air is fed to the ejector 14 and is supplied into the sterilizing chamber 1, permitting more improved uniformity of the temperature distribution in the sterilizing chamber 1 as well as reduction of time required in each temperature raising step.

Although the above embodiment has been described in relation to the sterilization of retort pouches, it will be appreciated that in sterilizing other packed foods, the second temperature raising step and the second sterilizing step may be omitted. The predetermined pressures and temperatures in the sterilizing chamber 1 in the temperature raising steps and the sterilizing steps as well as the time required for sterilization in the sterilizing steps may be suitably changed, depending upon the packed foods to be sterilized. In order to effect such changes, supply flow rates of steam and compressed air to the sterilizing chamber 1 and discharge rate of the mixture are adjusted by adjusting the throttle adjusting valves 16 and 18 in the bypass steam line 7, the throttle adjusting valve 30 in the bypass compressed air line 22 and the throttle adjusting valve 52 in the third branch pipe 48 of the drain line 43.

While the invention has been described with reference to a preferred embodiment thereof, it is to be understood that modifications or variations may be easily made without departing from the spirit of this invention which is defined by the appended claims.

What is claimed is:

1. Apparatus for sterilizing packed foods comprising:
a sterilizing chamber for storing packed foods therein;
a jet pipe mounted on the interior upper portion of said sterilizing chamber for jetting mixture of steam and compressed air;
an ejector having an inlet port, a suction port and an outlet port and connected at said outlet port to said jet pipe for generating a suction force through a flow of mixture of steam and compressed air;
a steam line connected to said inlet port of said ejector for supplying steam thereto;
a circulation line connected at one end to the interior lower portion of said sterilizing chamber and at the other end to said suction port of said ejector;
a drain line connected to the bottom of said sterilizing chamber for exhausting a part of the mixture of steam and compressed air;
a heat exchanger interposed between said sterilizing chamber and said drain line; and
a compressed air line connected to said inlet port of said ejector through said heat exchanger.

2. The apparatus as defined in claim 1 further comprising a pressure sensor mounted within said sterilizing chamber for detecting pressure in said sterilizing chamber and an exhaust valve connected to said drain line and operative to control the exhaust amount of the mixture in response to a detection signal from said pressure sensor so as to maintain said sterilizing chamber at a predetermined pressure.

* * * * *